United States Patent
Wu et al.

(10) Patent No.: US 11,432,756 B2
(45) Date of Patent: Sep. 6, 2022

(54) MULTI-CHANNEL REAL-TIME CARDIOVASCULAR PERFORMANCE EVALUATION SYSTEM AND METHOD CARDIOVASCULAR PERFORMANCE EVALUATION SYSTEM AND METHOD

(71) Applicants: Chi-Hua Foundation, New Taipei (TW); Tiffany Wu, New York, NY (US)

(72) Inventors: Wan-Lin Wu, New Taipei (TW); Hui-Wen Yang, New Taipei (TW); Men-Tzung Lo, New Taipei (TW)

(73) Assignees: Chi-Hua Foundation, New Taipei (TW); Tiffany Wu, New York, NY (US)

( * ) Notice: Subject to any disclaimer, the term of this patent is extended or adjusted under 35 U.S.C. 154(b) by 420 days.

(21) Appl. No.: 16/607,714

(22) PCT Filed: Apr. 9, 2019

(86) PCT No.: PCT/US2019/026414
§ 371 (c)(1),
(2) Date: Oct. 23, 2019

(87) PCT Pub. No.: WO2020/086112
PCT Pub. Date: Apr. 30, 2020

(65) Prior Publication Data
US 2021/0161456 A1    Jun. 3, 2021

Related U.S. Application Data

(60) Provisional application No. 62/750,044, filed on Oct. 24, 2018.

(51) Int. Cl.
*A61B 5/00* (2006.01)
*A61B 5/352* (2021.01)
(Continued)

(52) U.S. Cl.
CPC ............ *A61B 5/352* (2021.01); *A61B 5/0022* (2013.01); *A61B 5/327* (2021.01); *A61B 5/355* (2021.01); *A61B 5/366* (2021.01); *A61B 5/7225* (2013.01)

(58) Field of Classification Search
None
See application file for complete search history.

(56) References Cited

U.S. PATENT DOCUMENTS 8,396,538 B2 * 3/2013 Garner ................. A61B 5/304 600/509
8,433,395 B1 * 4/2013 Brockway ............. A61B 5/349 600/509

(Continued)

*Primary Examiner* — Shirley X Jian
(74) *Attorney, Agent, or Firm* — Chun-Ming Shih; HDLS IPR Services (57) ABSTRACT

A multi-channel real-time cardiovascular performance evaluation system, includes: a multi-channel ECG signals measurement unit, a multi-channel ECG signals processing device, and an ECG signals reconstruction unit. The method uses a MAMA-END algorithm, to mark ECG signals to replace the original ECG signal, and to extract characteristic peak value of the ECG signal. As such, the method is able to extract and reconstruct a first signal having QRS wave, and a second signal having T wave; then the method detects and marks the start of Q wave and the end of T wave on the first signal and the second signal. Therefore, the method is able to determine and evaluate if a patient does have cardiovascular disease, and to locate the lesion positions of a patient having cardiovascular disease.

9 Claims, 9 Drawing Sheets

(51) Int. Cl.
A61B 5/327 (2021.01)
A61B 5/355 (2021.01)
A61B 5/366 (2021.01)

(56) References Cited

U.S. PATENT DOCUMENTS

| | | | | |
|---|---|---|---|---|
| 8,571,645 B2* | 10/2013 | Wu | ......................... | A61B 5/364 600/517 |
| 8,632,465 B1* | 1/2014 | Brockway | .......... | H03H 17/0248 600/300 |
| 9,294,074 B2* | 3/2016 | Brockway | ................ | G06F 17/14 |
| 2002/0151806 A1* | 10/2002 | Starobin | ................. | A61B 5/349 600/509 |
| 2008/0114257 A1* | 5/2008 | Molin | ................... | A61N 1/3702 600/512 |
| 2009/0318821 A1* | 12/2009 | Demharter | ......... | G01R 33/5673 600/509 |

\* cited by examiner

MULTI-CHANNEL REAL-TIME CARDIOVASCULAR PERFORMANCE EVALUATION SYSTEM AND METHOD CARDIOVASCULAR PERFORMANCE EVALUATION SYSTEM AND METHOD

BACKGROUND OF THE INVENTION

Field of the Invention

The present invention relates to a cardiovascular performance evaluation system and method, and in particular to a multi-channel real-time cardiovascular performance evaluation system and method.

The Prior Arts

Among cardiovascular disease (CVD), coronary artery disease (CAD) is regarded as the main cause of a sudden death. The pathological changes caused by coronary artery disease (CAD) includes stenosis and even occlusion of coronary arteries for supplying oxygen and nutrients to the heart, thereby damaging cardiac tissues. Depending on the degree of severity, coronary artery disease (CAD) has different manifestations, namely angina, myocardial infarction, and sudden cardiac death. Angina is chest pain due to ischemia (a lack of blood, thus a lack of oxygen supply) of the heart muscle and typically occurs when the weather is cold or when the patient is mentally or physically overburdened or has an overstretched stomach. Myocardial infarction is worse than angina, because the underlying pathological change typical of myocardial infarction is irreversible damage of the heart muscle. Myocardial infarction ends up in a heart failure, when it is severe. In a worst-case scenario, the consequence of myocardial infarction is a sudden cardiac death, wherein the victim goes into shock and dies as soon as arrhythmia halts the heart and decreases the cardiac output greatly. Hence, coronary artery disease (CAD) is dubbed an invisible killer because of its symptomless insidious course. Coronary artery disease (CAD) is seldom diagnosed with a static electrocardiogram (static ECG), as it starts to alert a patient only when cardiac hypoxia happens to the patient.

At present, diagnosis tools in wide use for diagnosing coronary artery disease (CAD) include treadmill ECG, Thallium scan, and CT-angio However, the application of the aforesaid diagnosis tools is limited by size, costs, and the methodology of measurement, regardless of whether the diagnosis tools are used at hospital or at home. In this regard, the prognosis of coronary artery disease (CAD) is often evaluated by means of conventional ECG signals, albert with a drawback—providing just 12 channels which are restricted to longitudinal cross-sections and transverse cross-sections of the heart. Although the equipment required for providing the 12-channel ECG signals is simple and easy to operate, its spatial resolution is inadequate, not to mention that it provides a limited amount of information pertaining to the analysis and identification of related symptoms, thereby restricting its application and analysis. Furthermore, although high-resolution magnetocardiography (MCG) provides sufficient spatial information, it is not in wide use because of its high prices and large size.

Therefore, presently, there is a need to develop a non-radioactive cardiovascular performance evaluation system and method, that is capable of raising spatial resolution of electrocardiogram (ECG) signals, while achieving reduced cost and diminished size. As such, this system and method can be used to analyze, evaluate, and determine more accurately real time if a patient does have cardiovascular disease (CVD), to correctly locate the lesion position of cardiovascular disease (CVD).

SUMMARY OF THE INVENTION

In view of the problems and drawbacks of the prior art, the present invention provides a multi-channel real-time cardiovascular performance evaluation system and method. The multi-channel real-time cardiovascular performance evaluation method is realized through using the multi-channel real-time cardiovascular performance evaluation system, that mainly includes the following:

a multi-channel ECG signals measurement unit, adapted to be used to detect and measure ECG signals for different spatial positions of cardiovascular. The ECG signals include P wave, Q wave, R wave, S wave, and T wave;

a multi-channel ECG signals processing device, connected to the multi-channel ECG signals measurement unit, to receive the ECG signals therefrom, and input the received ECG signals into an internal circuit of the device, to perform reconstruction of the ECG signals; and an ECG signals reconstruction unit, disposed on the internal circuit of the multi-channel ECG signals processing device. An electrocardiogram (ECG) extracted wave reconstruction method is stored in the ECG signals reconstruction unit, that is referred to as a MAMA-EMD algorithm, and it includes the following steps:

Step 1: adding a masking signal to the original ECG signals to derive the composite signal, to filter out high frequency noise;

Step 2: determining and marking the first characteristic peak point of the composite signals;

Step 3: utilizing a de-peak function to smooth out the composite signal, to replace the first characteristic peak point of the composite signals;

Step 4: performing waveform comparisons for the waveforms obtained in the step 2 and step 3, to remove baseline drift from the composite signals, to obtain a first signal having the first characteristic peak;

Step 5: determining and marking the results of waveform comparisons of step 4, to extract the second characteristic peak point from the remaining ECG signal;

Step 6: utilizing another de-peak function to smooth out the remaining ECG signal, to replace the second characteristic peak point of the ECG signals; and Step 7: performing waveform comparisons for the waveforms obtained in the step 5 and step 6, to obtain a second signal having the second characteristic peak.

Preferably, the first signal is a complex wave signal having Q, R, S waves, but the present invention is not limited to this. The start of Q wave is the first local maximum value before each R peak.

Preferably, the second signal is a T wave signal, but the present invention is not limited to this. The end point of T wave is set to be the last point above the threshold value.

Through utilizing the MAMA-EMD reconstruction algorithm, the multi-channels ECG signals having different spatial positions can be obtained. As such, the time points of the first signal having the reconstructed QRS wave, the second signal having T wave, the start of Q wave, and the end of T wave can be separated effectively. In this approach, the multi-channel real-time cardiovascular performance evaluation system of the present invention is able to evaluate more accurately real time the functions and performance of the cardiovascular, to determine if a patient does have cardiovascular disease, and to locate more correctly the lesion positions of a patient having cardiovascular disease.

Further scope of the applicability of the present invention will become apparent from the detailed descriptions given hereinafter. However, it should be understood that the detailed descriptions and specific examples, while indicating preferred embodiments of the present invention, are given by way of illustration only, since various changes and modifications within the spirit and scope of the present invention will become apparent to those skilled in the art from the detailed descriptions.

BRIEF DESCRIPTION OF THE DRAWINGS

The related drawings in connection with the detailed descriptions of the present invention to be made later are described briefly as follows, in which.

DETAILED DESCRIPTION OF THE PREFERRED EMBODIMENT

The purpose, construction, features, functions and advantages of the present invention can be appreciated and understood more thoroughly through the following detailed descriptions with reference to the attached drawings.

Figure 1:
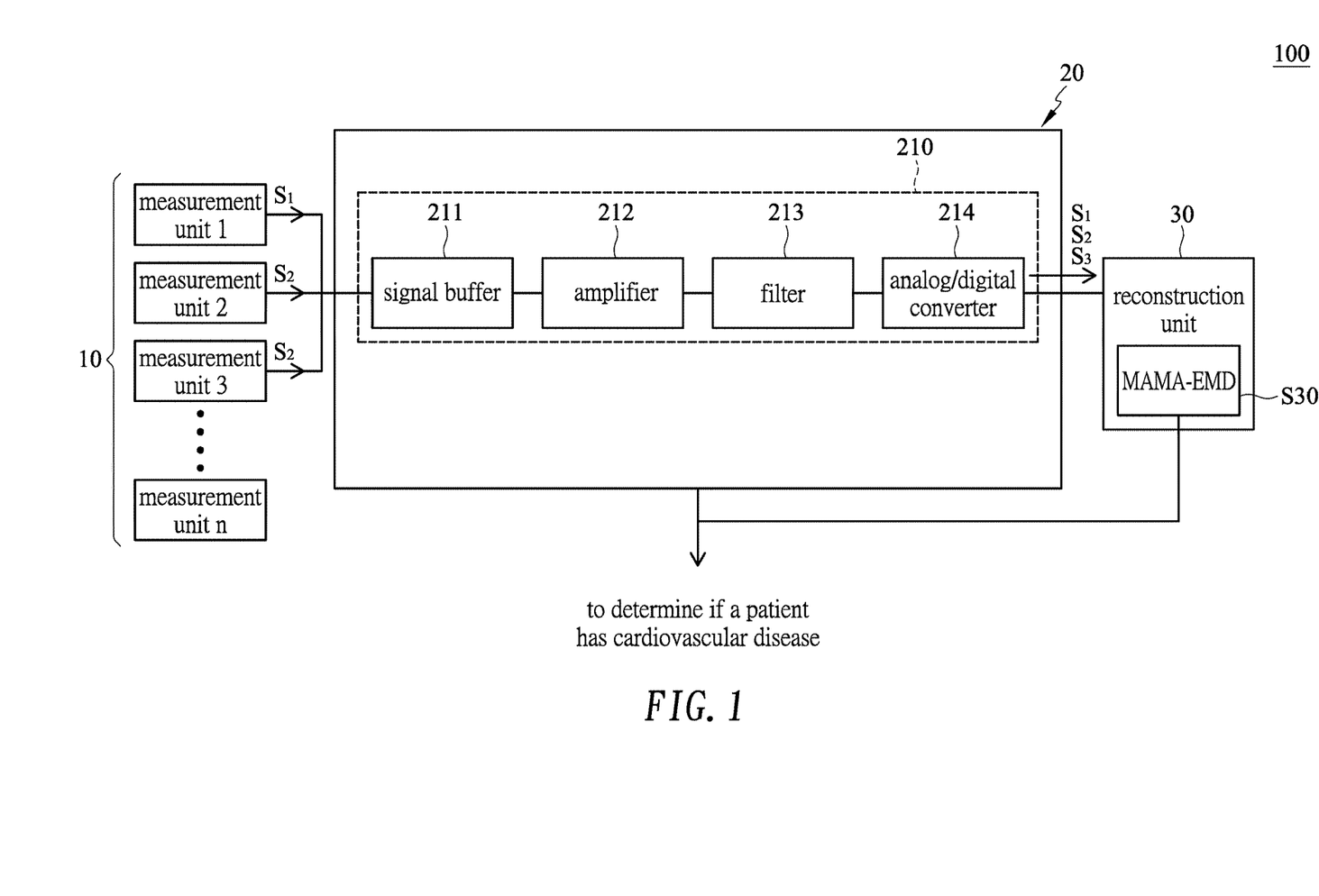
FIG. 1 is a block diagram of a multi-channel real-time cardiovascular performance evaluation system according to an embodiment of the present invention.
Figure 2:
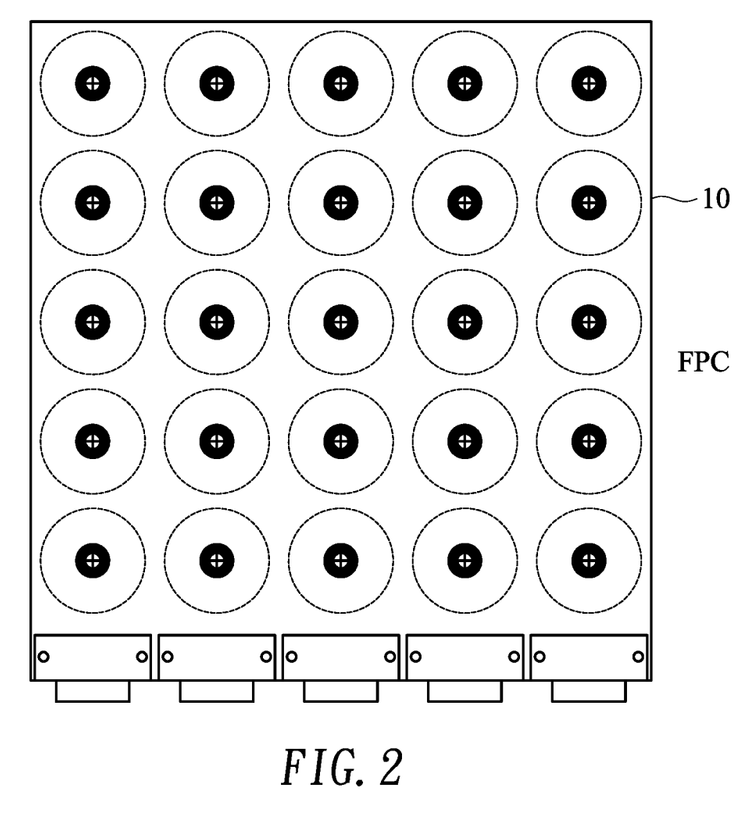
FIG. 2 is a top view of multi-channel ECG signals measurement unit according to an embodiment of the present invention.
Figure 3:
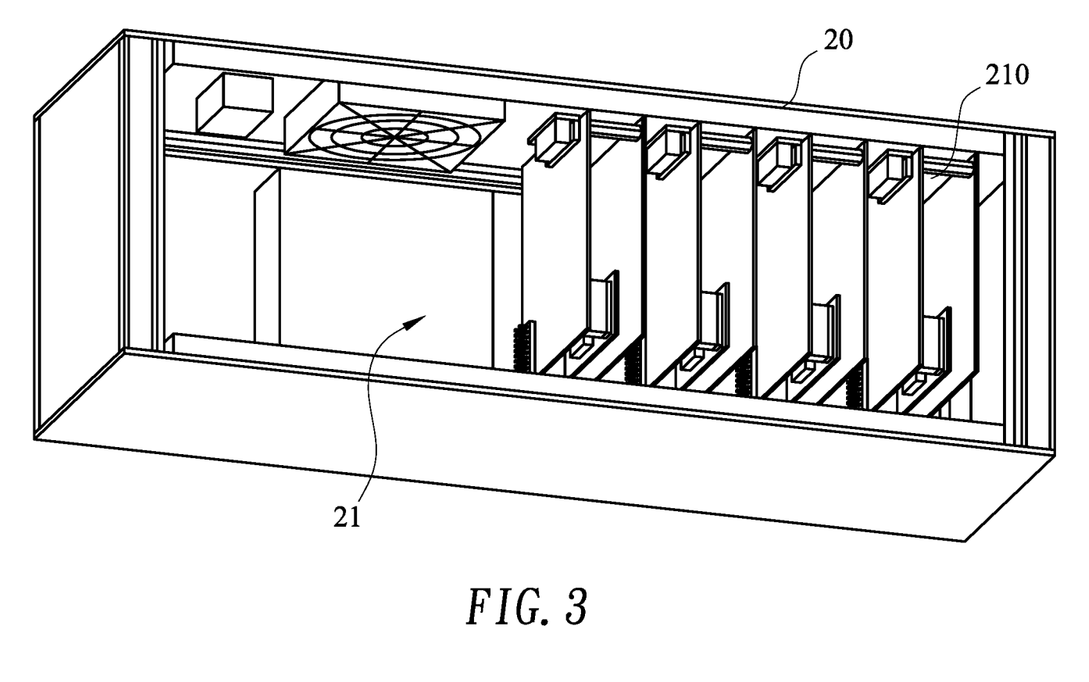
FIG. 3 is a top view of multi-channel ECG signals processing device according to an embodiment of the present invention.
Figure 4:
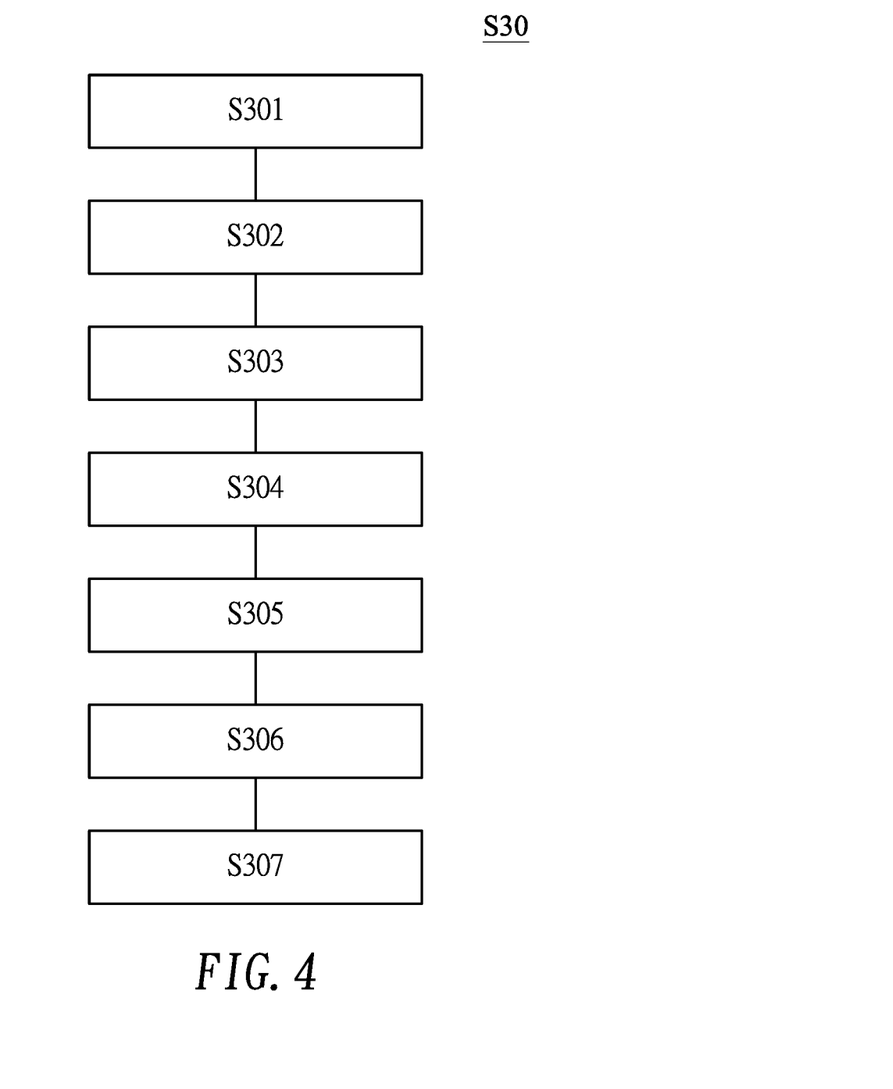
FIG. 4 is a system flowchart of a multi-channel real-time cardiovascular performance evaluation method according to an embodiment of the present invention.
Figure 5:
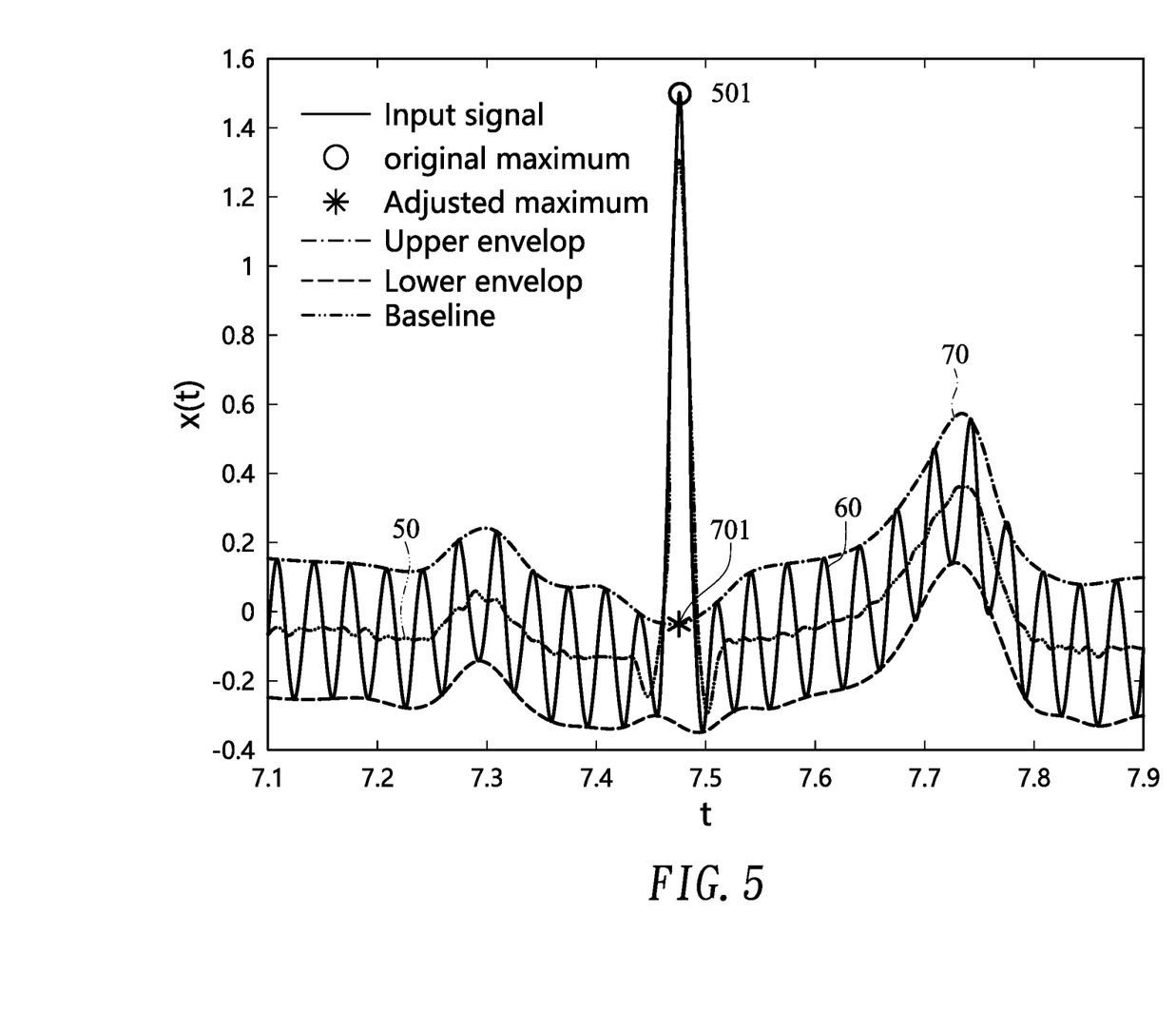
FIG. 5 is a waveform diagram of the processing for extracting the first signal by using an MAMA-EMD algorithm according to an embodiment of the present invention.
Figure 6:
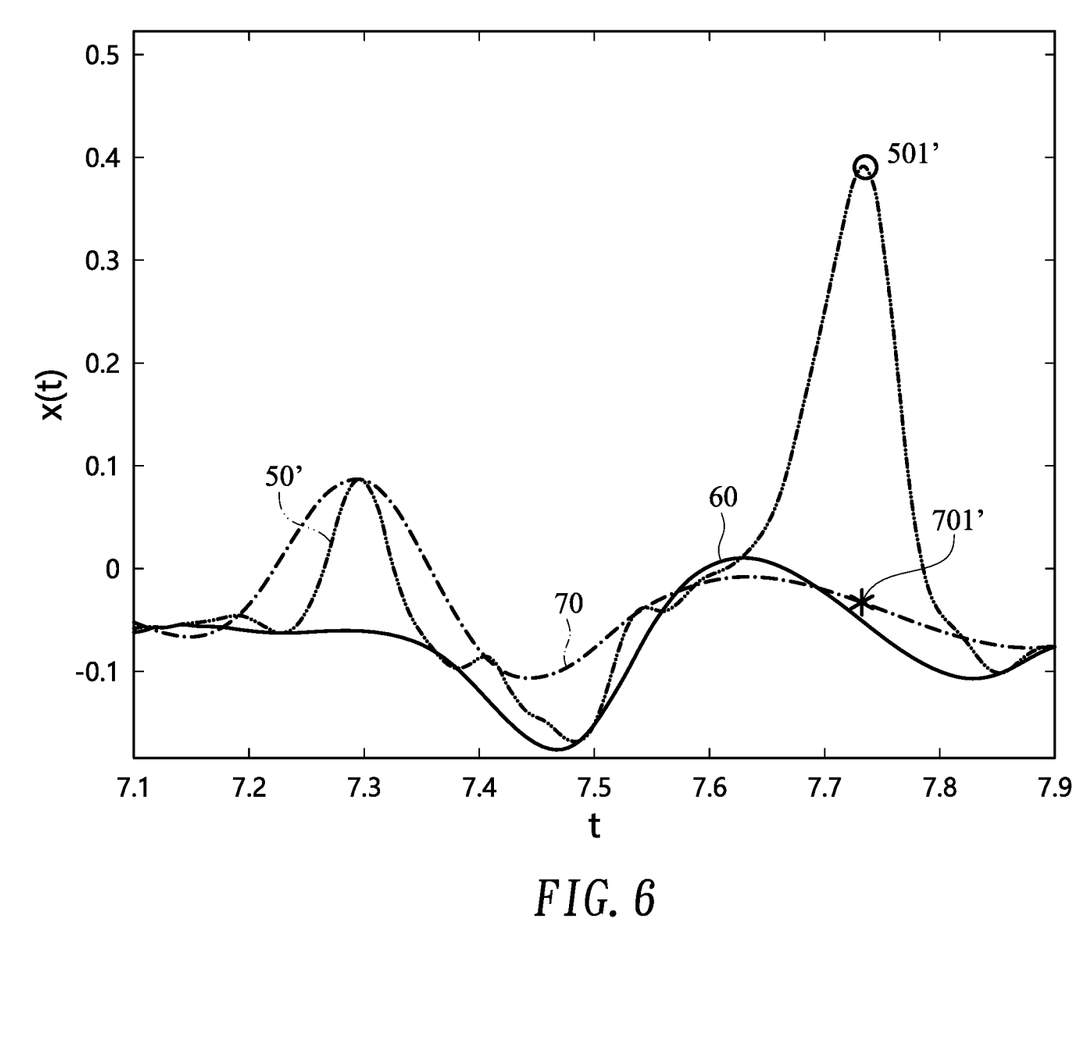
FIG. 6 is a waveform diagram of the processing for extracting the second signal by using a MAMA-EMD algorithm according to an embodiment of the present invention.
Figure 7A:
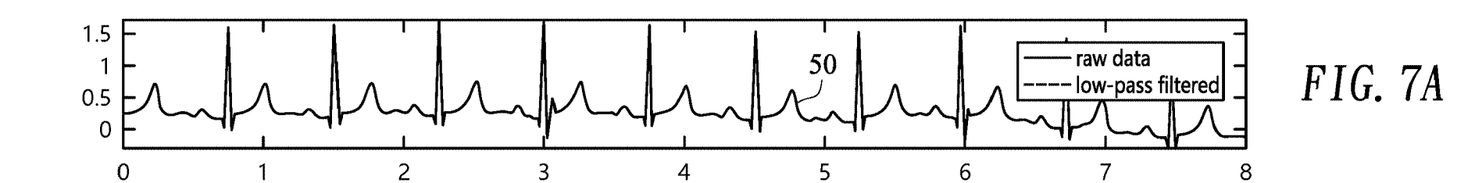
FIGS. 7A to 7E are waveform diagrams of waveforms of the extracted T wave and QRS wave according to an embodiment of the present invention.
Figure 7B:
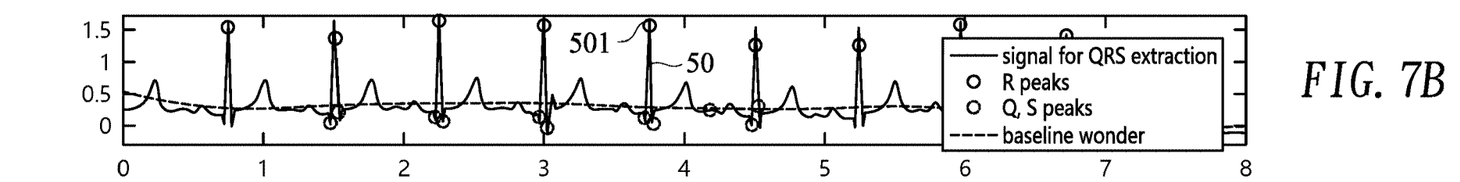
Figure 7C:
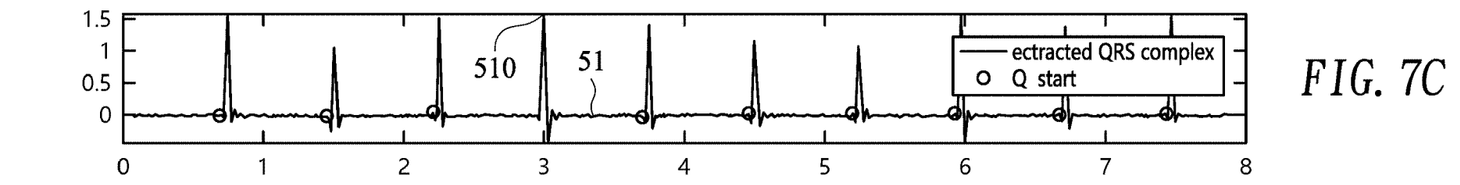
Figure 7D:
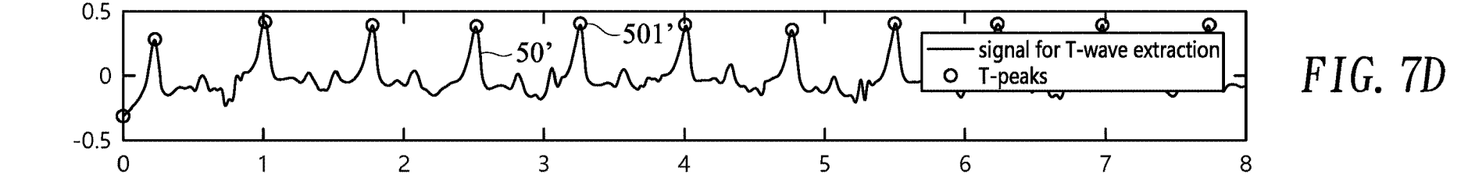
Figure 7E:
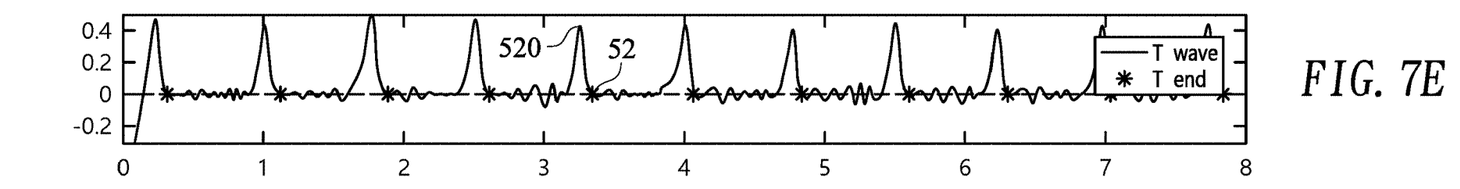

Refer to FIGS. 1 to 7E respectively for a block diagram of a multi-channel real-time cardiovascular performance evaluation system according to an embodiment of the present invention; a top view of multi-channel ECG signals measurement unit according to an embodiment of the present invention; a top view of multi-channel ECG signals processing device according to an embodiment of the present invention; a system flowchart of a multi-channel real-time cardiovascular performance evaluation method according to an embodiment of the present invention; a waveform diagram of the processing for extracting the first signal by using a MAMA-EMD algorithm according to an embodiment of the present invention; a waveform diagram of the processing for extracting the second signal by using a MAMA-EMD algorithm according to an embodiment of the present invention; and waveform diagrams of waveforms of the extracted T wave and QRS wave according to an embodiment of the present invention;

As shown in FIGS. 1 to 7E, the present invention provides a multi-channel real-time cardiovascular performance evaluation system 100 mainly includes the following:

a multi-channel ECG signals measurement unit 10, adapted to be used to detect and measure ECG signals 50 for different spatial positions of the heart. The ECG signals may include P waves, Q waves, R waves, S waves, and T waves;

a multi-channel ECG signals processing device 20, connected to the multi-channel ECG signals measurement unit 10, to receive the ECG signals therefrom, and input the received ECG signals 50 into an internal circuit 21 of the device, to perform reconstruction of the ECG signals;

an ECG signals reconstruction unit 30, disposed on the internal circuit 21 of the multi-channel ECG signals processing device 20. An electrocardiogram (ECG) extracted wave reconstruction method is stored in the ECG signals reconstruction unit 30, that is referred to as a MAMA-EMD algorithm S30, and it includes the following steps:

Step S301: adding a masking signal to the original ECG signals 50 to derive the composite signal 60, and filter out high frequency noises, as shown in FIG. 5;

Step S302: determining and marking the first characteristic peak point 501 of the composite signals 60 and;

Step S303: utilizing a de-peak function to find a smooth curve 70 and its corresponding point 701, to replace the first characteristic peak point 501 of the composite signal 60;

Step S304: performing waveform comparisons for the waveforms obtained in the step S302 and step S303, to remove baseline drift from the composite signals 60 and the smooth curve 70, to obtain a first signal 51 having the first characteristic peak point 510, as shown in FIG. 7C;

Step S305: determining and marking the results of waveform comparisons of step S304, to extract the second characteristic peak point 501' from the remaining ECG signal 50', as shown in FIG. 6;

Step S306: utilizing another de-peak function to find a smooth curve 70 and its corresponding point 701', to replace the second characteristic peak point 501' of the remaining signal; and Step S307: performing waveform comparisons for the waveforms obtained in the step S305 and step S306, to obtain a second signal 52 having the second characteristic peak point 520, as shown in FIG. 7E.

Preferably, the first signal 51 is a complex wave signal having Q, R, S waves, but the present invention is not limited to this. The start of Q wave is the first local maximum value before each R peak Preferably, the second signal 52 is a T wave signal, but the present invention is not limited to this. The end point of T wave is set to be the last point above the threshold value.

Through utilizing the MAMA-EMD reconstruction algorithm, the multi-channels ECG signals having different spatial positions can be obtained. As such, the time points of the first signal of the reconstructed QRS wave, the second signal of T wave, the start of Q wave, and the end of T wave can be separated effectively. In this approach, the multi-channel real-time cardiovascular performance evaluation system of the present invention is able to evaluate more accurately real time the functions and performance of the heart, to determine if a patient does have cardiovascular disease, and to locate more correctly the lesion positions of a patient having cardiovascular disease.

Preferably, in the step S301 above, the masking signal is a masking-EMD having frequency of 250 Hz. In the step S302 above, the determined and marked first characteristic peak point 501 includes maximum peak values $G^{M1}$ and minimum peak values $G^{N1}$. The wave of the maximum peak value is a R wave; while the wave of minimum peak value is a Q wave, a S wave, or other type waves. In the step S303 above, the replacement is applied on the signals having peak values of $G^{M1}$ and $G^{N1}$.

In the step S305 above, the determined and marked second characteristic peak point 501' includes a maximum peak value $G^{M2}$, that is greater than the threshold value (namely, the T wave peak value), and is a T wave. In the step S306 above, the replacement is applied on the signals having peak values of $G^{M2}$.

In the following, the MAMA-EMD reconstruction algorithm S30 is described in further details.

Firstly, adding a masking signal to a signal such as an ECG signal 50, to form a composite signal 60.

Next, utilizing a threshold value T and a window size D, to detect and determine the peak value $G^M$ and $G^N$ of the input signal.

Then, starting to decompose the first intrinsic mode function (IMF).

Subsequently, in the sifting of the first IMF, using a Minimum Arc Length Method (the details of which will be described later), to adjust various extrema points in subset $G^M$ and $G^N$.

Given a signal x(t) (t>0), we define k as the IMF index and p the sifting step.

Then, the notation $x^{k,p}$ represents the $k_{th}$ proto-IMF at $p_{th}$ sifting step. After k sifting steps, the first proto-IMF having peaks can be extracted.

Finally, repeating the steps above on input signals having the first-IMF removed from the original signal, to derive other proto-IMFs.

In the following, the MAMA-EMD reconstruction algorithm S30 is described in more details.
(1) Generate masking signal $w(t)=a_M \sin(2\pi f_M t)$
(2) Let $x^+(t)=x(t)+w(t)$
(3) Define $x^{0,0} \triangleq x^+(t)$. Start with k=1 and p=0. Set $x^{1,0}(t)=x(t)$.
(4) Identify all the maxima $\{(t_a, x_a)\}$ and minima $\{(t_b, x_b)\}$ of $x^{k,0}(t)$
(5) Start with a=1 and set up threshold T and window size D. Apply Formula (8) and (9) to find the subset of maximum impulses $G^M=\{(t_{a_i}, x_{a_i})\}$, i=1 ... $n_{spx}$, and also find the subset of minimum impulses $G^N=\{(t_{b_j}, x_{b_j})\}$, j=1 ... $n_{spn}$. Here, $n_{spx}$ and $n_{spn}$ are the total number of points regarded as maximum impulses and minimum impulses, respectively.
(6) Start with i=1, find minimizer $\{(t_{a_i}, \hat{x}_{a_i})\}$ to minimize the arc length of upper envelope $U(t|x_a)$.
(7) Substitute $\{(t_{a_i}, x_{a_i})\}$ with $\{(t_{a_i}, \hat{x}_{a_i})\}$, and form the new set of maximum points $\{(t_a, \hat{x}_a)\}$.
(8) Repeat (6) and (7) for i=2 ... $n_{spx}$.
(9) For each j=1 ... $n_{spn}$, find minimizers $\{(t_{b_j}, \hat{x}_{b_j})\}$ to minimize the arc length of lower envelope $L(t|x_b)$, consecutively. Then, replace $\{(t_{b_j}, x_{b_j})\}$ with $\{(t_{b_j}, \hat{x}_{b_j})\}$. Form the new set of minimum points $\{(t_b, \hat{x}_b)\}$.
(10) Derive the new upper and lower envelope $U(t|\hat{x}_a)$ and $L(t|\hat{x}_b)$, respectively, according to the new set of maxima $\{(t_a, \hat{x}_a)\}$ and minima $\{(t_b, \hat{x}_b)\}$.
(11) Obtain the local mean of the upper and lower envelopes $m(t)=(U(t)+L(t))/2$
(12) Subtract local mean from the temporal signal $x^{1,p+1}(t)=x^{1,p}(t)-m(t)$
(13) Repeat steps (4)-(11) for p=1 ... $n_{sf}-1$, where $n_{sf}$ is the number of sifting. Derive the first proto-IMF $x^{1+}(t)=x^{1,n_{sf}}$
(14) Let $x^-(t)=x(t)+w(t)$. Let $x^{0,0}=x^-(t)$. Repeat steps (3)-(13) to derive $x^{1-}(t)$.
(15) The resultant IMF1 is defined as $c_1=(x^{1+}(t)+x^{1-}(t))/2$. For k>1, the steps are the same as the original EMD.

In an embodiment of the present invention, refer to FIGS. 5 and 6, the "Minimum Arc Length Method" and the "Spike Definition and Detection" are described respectively as follows:

A. Minimum Arc Length Method

We aim to find an optimal replacement of the extrema value while maintaining the position of it as a knot (FIG. 5). In this way, the magnitude of the impulse response of spike point to the rest of the point is decreased. On the aspect of time domain, the estimated upper/lower envelope would be smoother, and so does the mean envelope, m(t). Thus, the morphology of the spike would be retained in the first IMF. We propose to minimize the arc length of the resultant upper or lower envelope.

Here, we take the upper envelope as an example to illustrate our method; the lower envelope is processed similarly. Given a signal x(t) (t>0) with the series of local maxima $\{(t_a, x_a)\}$, a=1 ... N, the upper envelope $U(t|x_a)$ is the cubic spline connecting through all $\{(t_a, x_a)\}$. If the maximum point of an impulse is $(t_{a_s}, x_{a_s})$, we choose $(t_{a_s}, \hat{x}_{a_s})$ according to $$\hat{x}_{a_s}=\arg\min_y\{F(U(t|y_a=x_a, a\neq a_s; y_{a_s}=y))\} \quad \text{(Eq. 1)}$$

where $$F(U(t|\cdot))=\int_0^{t_N}\sqrt{1+\left(\frac{dU(t|\cdot)}{dt}\right)^2}\,dt \quad \text{(Eq. 2)}$$

is the arc length of $U(t|\cdot)$. Then, the modified spline is created by the new series of maxima with impulse point replaced by $(t_{a_s}, \hat{x}_{a_s})$. For signals with more than one impulse point, each impulse point will be replaced consecutively.

As shown in FIG. 5, the input signal x(t) (black) is first processed to detect spike points $(t_{a_s}, x_{a_s})$ (o). Then, the height of this point is adjusted to become a new knot $(t_{a_s}, \hat{x}_{a_s})$ (*) that minimizes the arc length of the upper envelope. The new upper envelope U(t) (blue) is calculated by the new knot and the other original extrema. This creates a baseline m(t) (green) that is smooth and depicts the relatively low frequency of the signal.

B. Spike Definition and Detection

We adopted one of the simplest designs, the median filter to detect spikes. Mathematically, a signal with occasional artifacts can be modeled as $$x(t)=\hat{x}(t)+v(t) \quad \text{(Eq. 3)}$$

where $\hat{x}(t)$ is the signal of interest, v(t) models the noise term and x(t) is the observed signal. We suggest that the noise term contains two components $$v(t)=\omega(t)+z(t)i(t) \quad \text{(Eq. 4)}$$

where $\omega(t)$ represents the white Gaussian process, i(t) is the random process generating impulsive artifact and z(t) models the impulsive noise as a heavy-tailed white noise.

Similar to other impulse detection algorithms, our spike detector is based on the prior assumption that the signal should be smoothly varying. Therefore, the extrema that differ too much from nearby extrema is regarded as spike points. The maximum and minimum were dealt separately. We first explain our protocol in the example of maxima, and the minimum is processed in the similar way. For each maximum $\{(t_{a_i}, x_{a_i})\}$, we first find the subset of D nearby maximum values in a window centered about it (D is an even value).

$$W_i^D = \{x_{a_j} | i - D/2 \le j \le i + D/2\} \quad \text{(Eq. 5)}$$

The median value and standard deviation of this subset are $$m_i^D = \text{Med}\{x_{a_j} | x_{a_j} \in W_i^D\} \quad \text{(Eq. 6)}$$

and $$S_i^D = \text{std}\{x_{a_j} | x_{a_j} \in W_i^D\} \quad \text{(Eq. 7)}$$

respectively. Then, the extrema values that are T times larger than the standard deviation is classified as the maximum impulses, i.e. the subset of maximum impulses is defined as $$G^M = \{(t_{a_i}, x_{a_i}) | x_{a_i} > m_i^D + S_i^D \cdot T\} \quad \text{(Eq. 8)}$$

Similarly, the subset of minimum impulses is defined as $$G^N = \{(t_{b_s}, x_{b_s}) | x_{b_i} < m_i^K - S_i^K \cdot T\} \quad \text{(Eq. 9)}$$

Where $m_i^K$ and $S_i^K$ are median and standard deviation of the minimum values within the window $W_i^K$ centered at $x_{b_i}$. Finally, these points in the subsets $G^M$ and $G^N$ will be re-adjusted consecutively for the subsequent analysis.

In an embodiment, refer to FIGS. 1, 7A to 7E, for which the descriptions above can be applied on QT wave extraction as follows:
(a) Filter the high frequency noise by applying masking-EMD with masking frequency equals to 250 Hz. (FIG. 7A)
(b) Detect maximum peaks, $G^{M_1}$, and minimum peaks, $G^{N_1}$. The maximum peaks are the R waves, and the minimum peaks are the Q, S and some other. (FIG. 7B)
(c) Apply MAMA-EMD on the signal with the $G^{M_1}$ and $G^{N_1}$ as spikes.
(d) The signal with QRS complexes is extracted. The Q start is the first local maximum before each R peak. (FIG. 7C)
(e) Remove baseline wonder.
(f) Detect maximum peaks, $G^{M_2}$, above a threshold, i.e. the T-peak. (FIG. 7D)
(g) Apply MAMA-EMD on the signal with T-peaks as spikes.
(h) The T-waves are extracted, isolated from the signal. (FIG. 7E)
(i) The end of T-wave is set as the last point above a threshold (FIG. 7E)

It is worth to note that, in the present invention, the MAMA-EMD reconstruction algorithm S30 used for extracting the ECG signal can be realized in a hardware circuit or by a software package.

Figure 8:
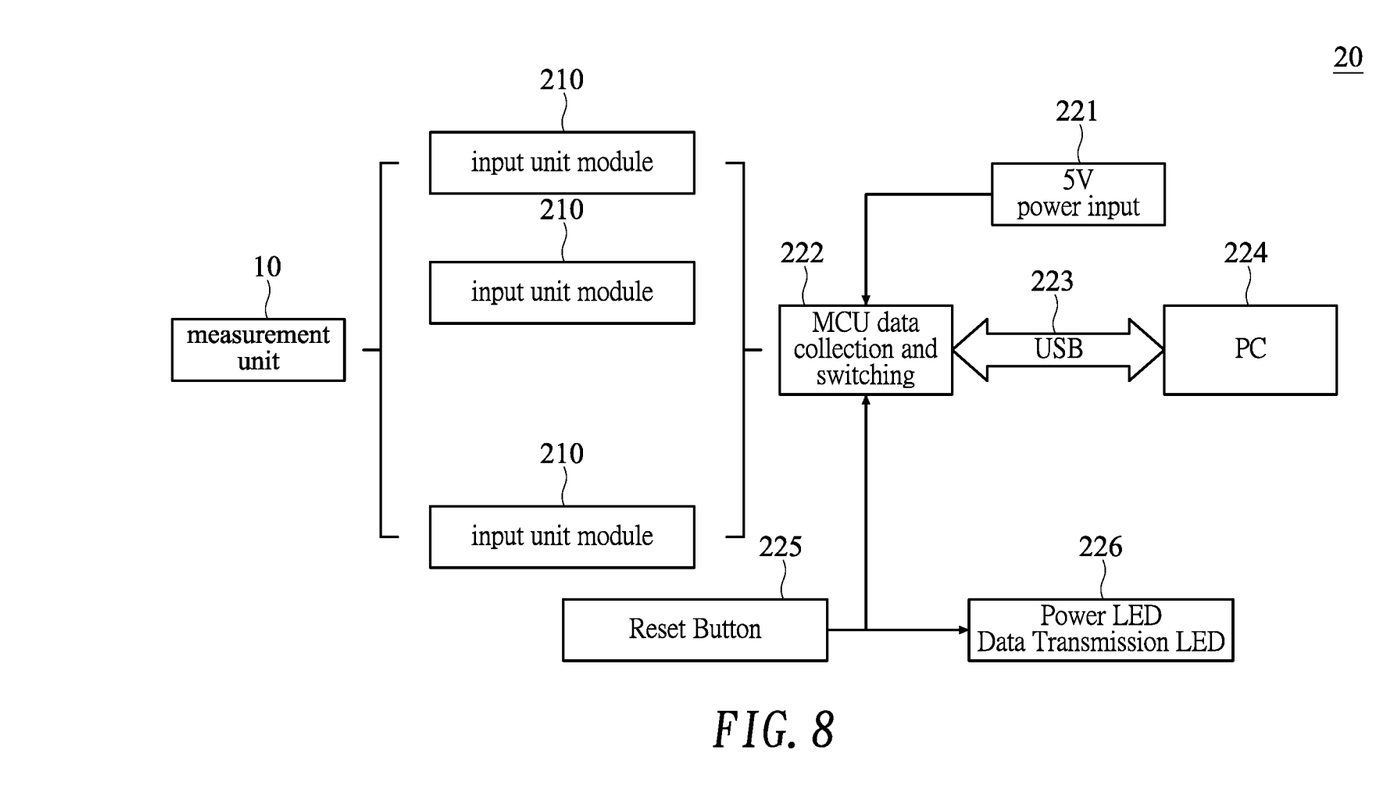
FIG. 8 is a circuit block diagram of the multi-channel ECG signals processing device according to an embodiment of the present invention.

Refer to FIGS. 1, 8 in an embodiment, the present invention provides a multi-channel real-time cardiovascular performance evaluation system 100. Wherein, the internal circuit 21 of the multi-channel ECG signals processing device 20 is provided with four input unit modules 210. And each input unit modules 210 is formed a signal buffer 211, an amplifier 212, a filter 213, and a digital/analog converter 214 connected in series. Further, each input unit modules 210 is connected to a 5V power input 221, an MCU data collection and switching 222, a USB 223, PC 224, reset button 225, and Power LED Data Transmission LED 226. The PC 224 is outside of the system.

The signal buffer 211 provides a sufficiently large input impedance, to match and couple the weak ECG signal detected to the amplifier 212. The amplifier 212 receives the weak ECG signal and amplifies it to a sufficiently large ECG signal. The filter 213 is used mainly to remove baseline drift for the ECG signal, high frequency noise, and interference of power signal. The band pass frequency range for the filter 213 is 0.5 Hz-150 Hz, while the band rejection frequency is 60 Hz. After filtering, the ECG signal is sent to the digital/analog signal converter 214 for converting it into digital signals, for the subsequent use of the reconstruction unit 30.

Figure 9:
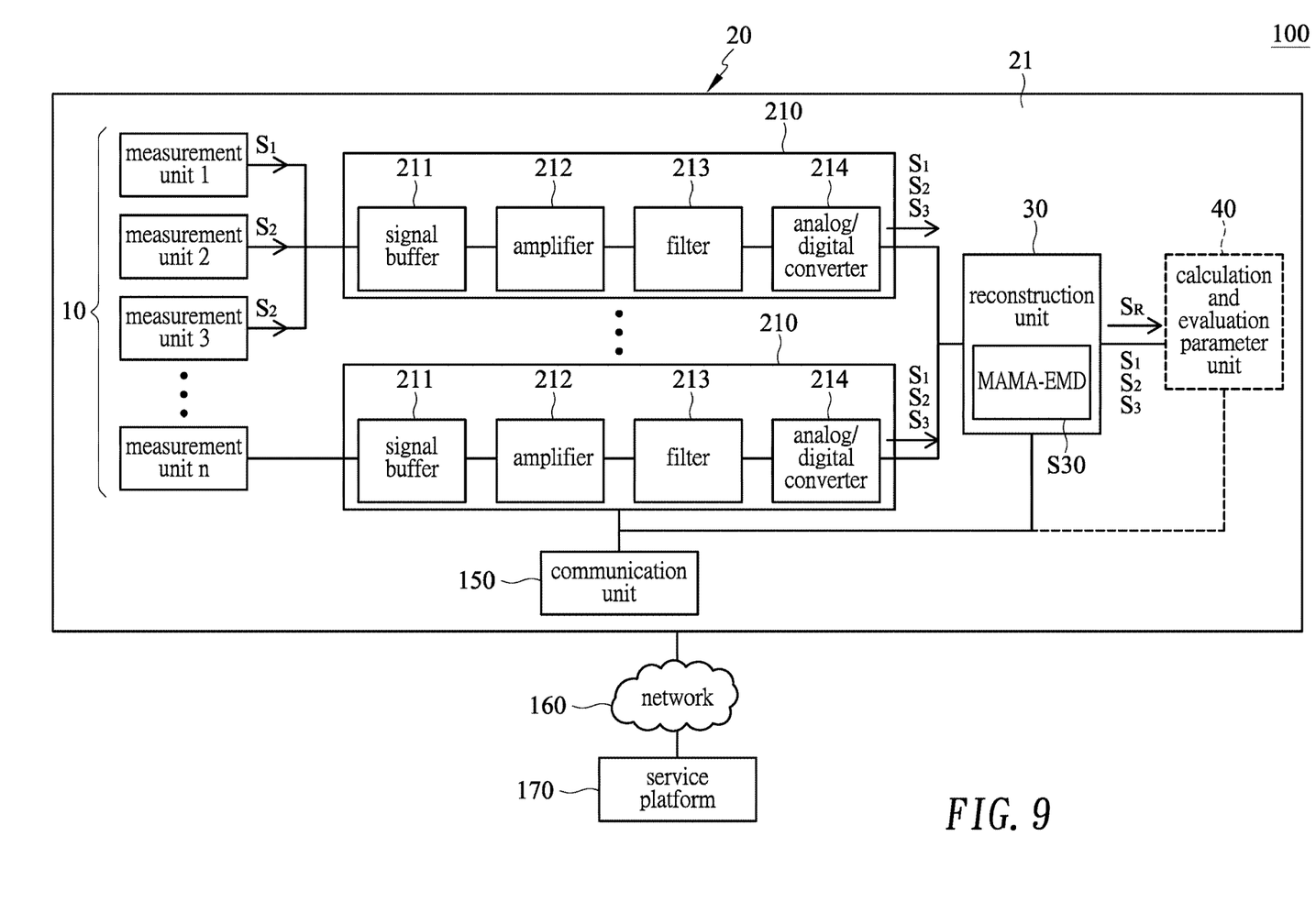
FIG. 9 is a block diagram of a multi-channel real-time cardiovascular performance evaluation system according to another embodiment of the present invention.

In another embodiment, as shown in FIG. 9, a calculation and evaluation parameter unit 40 can be placed in the multi-channel ECG signals processing device 20 to save space, to determine more accurately if a patient does have cardiovascular disease, and to locate more precisely the lesion positions of a patient having cardiovascular disease. Also, the ECG signals reconstruction unit 30 can be placed in the multi-channel ECG signals processing device 20, to save space. Further, a communication unit 150 can be disposed in the multi-channel ECG signals processing device 20, to be connected in a wired or wireless manner to a remote service platform 170 through a network 160, to provide related data synchronously to the medical units, for the reference of remote diagnoses.

The above detailed description of the preferred embodiment is intended to describe more clearly the characteristics and spirit of the present invention. However, the preferred embodiments disclosed above are not intended to be any restrictions to the scope of the present invention. Conversely, its purpose is to include the various changes and equivalent arrangements which are within the scope of the appended claims.

What is claimed is:

1. A multi-channel real-time cardiovascular performance evaluation method, adapted to construct a multi-channel real-time cardiovascular performance evaluation system, the system comprising:
a multi-channel ECG signal measurement unit, used to detect and measure ECG signals for different spatial positions of a heart, wherein the ECG signals have P waves, Q waves, R waves, S waves, and T waves;
a multi-channel ECG signal processing device, connected to the multi-channel ECG signal measurement unit, and to input the ECG signals that are measured into an internal circuit of the device, for reconstructing the ECG signals that are measured; and
an ECG signal reconstruction unit, disposed on the internal circuit of the multi-channel ECG signal processing device, an electrocardiogram (ECG) extracted wave reconstruction module being stored in the ECG signal reconstruction unit, that is referred to an MAMA-EMD firmware,
the multi-channel real-time cardiovascular performance evaluation method comprising steps of:
step 1: adding a masking signal to the ECG signals, to filter out high frequency noises;
step 2: determining and marking a first characteristic peak point of the ECG signals with the masking signal;
step 3: utilizing an MAMA-EMD de-peak function to smooth out the ECG signals, in order to replace the first characteristic peak point of the ECG signals with the masking signal;
step 4: performing waveform comparisons with results obtained in the step 2 and step 3, in order to remove baseline drift from the ECG signals with the masking signal, and obtain a first signal having the first characteristic peak point;
step 5: determining and marking the results of the waveform comparisons in the step 4, to extract a second characteristic peak point of remaining signals filtered by the MAMA-EDA firmware;

step 6: utilizing the MAMA-EMD de-peak function to smooth out the ECG signals to replace the second characteristic peak point of the remaining signals; and step 7: performing waveform comparisons with results obtained in the step 5 and step 6, to remove baseline drift from the remaining signals, and to obtain a second signal having the second characteristic peak point;

wherein through utilizing separate time points of the first signal of a reconstructed QRS wave, the second signal of the T waves, the start of the Q waves, and the end of the T waves, the multi-channel real-time cardiovascular performance evaluation system determined whether there is a cardiovascular disease;

wherein the MAMA-EMD reconstruction firmware used for reconstructing the ECG signals is realized in a hardware circuit.

2. The multi-channel real-time cardiovascular performance evaluation method as claimed in claim 1, wherein
the first signal is a complex wave signal having the Q waves, the R waves, and the S waves, a start of the Q waves being a first local maximum value before each peak of the R waves;
the second signal is a T wave signal, an end point of the T waves being set to be a last point above a threshold value.

3. The multi-channel real-time cardiovascular performance evaluation method as claimed in claim 2, wherein in the step 1, the masking signal is a masking-EMD with a frequency of 250 Hz; in the step 2, the determined and marked first characteristic peak point includes a first maximum peak value and a minimum peak value, the wave of the first maximum peak value being the Q waves, and the wave of the minimum peak value is the Q waves and the S waves, the step 3 replacing signals with the first maximum peak value and the minimum peak value.

4. The multi-channel real-time cardiovascular performance evaluation method as claimed in claim 3, wherein the second characteristic peak point in the step 5 includes a second maximum peak value, waves of the second maximum peak value being the T waves that are greater than the threshold value, the step 6 replacing with the second maximum peak value.

5. The multi-channel real-time cardiovascular performance evaluation method as claimed in claim 4, further comprising steps of:
step 1', the masking signal being a masking-EMO with a frequency of 250 Hz, in order to remove the high frequency noises;
step 2', the determined and marked first characteristic peak point including a first maximum peak value and a minimum peak value, waves of the maximum peak value being the Q waves, and the wave of the minimum peak value being the Q waves and the S waves;
step 3', the MAMA-EMD de-peak function to smooth out ECG signals being applied to signals with the first maximum peak value and the minimum peak value $G^{N1}$;
step 4', extracting the complex signal having the Q waves, the R waves and the S waves, the start of the Q waves is the first local maximum value before each peak of the R peak values, removing the baseline drift;
step 5', the extracted remaining signal having a second maximum peak value that is greater than the threshold value;

step 6', the MAMA-EMD de-peak function to smooth out ECG signals being applied to signals with a T wave peak value; and step 7', extracting the T wave peak value in order to separate it from the signals, and setting an end point of the T wave peak value as the last point above the threshold value.

6. The multi-channel real-time cardiovascular performance evaluation method as claimed in claim 5, further comprising steps of:
step 1", utilizing the threshold value and a window size D to detect and determine peak points $G^M$ and $G^N$ of the signals from the step 2' to the step 4';
step 2", decomposing a first intrinsic mode function (IMF);
step 3", during a sifting of the first IMF, using a Minimum Arc Length Method of the MAMA-EMD de-peak function to smooth out the ECG signals to readjust various points in subsets $G^M$ and $G^N$;
step 4", utilizing a signal x(t) (t>0), and defining k as an IMF index and p as a sifting step; notation $x^{k,p}$ representing a $k_{th}$ proto-IMF at $p_{th}$ shifting step, after k sifting steps, extracting a first proto-IMF having peak values; and
step 5", repeating the steps above of other input signals having the masking signal being removed from the ECG signals, to derive other proto-IMFs; and
step 6", the first proto-IMF is an average of two other proto-IMFs, and using the MAMA-EMD firmware to de-compose the remaining IMFs.

7. A multi-channel real-time cardiovascular performance evaluation system, comprising:
a multi-channel ECG signal measurement unit, adapted to detect and measure ECG signals for different spatial positions of a heart, wherein the ECG signals have P waves, Q waves, R waves, S waves, and T waves;
a multi-channel ECG signal processing device, having at least an input port and an internal circuit connected thereto, connected to the multi-channel ECG signal measurement unit, to receive the ECG signals therefrom and inputting the ECG signals into the internal circuit, to perform sequent reconstruction of the ECG signals; and
an ECG signal reconstruction unit, disposed on the internal circuit of the multi-channel ECG signal processing device, an MAMA-EMD firmware being stored in the ECG signal reconstruction unit to reconstruct the ECG signal, an MAMA-EMD de-peak function to smooth out ECG signals replacing a characteristic peak point of the ECG signals with a masking signal, to reconstruct and obtain a first signal having the Q waves, the R waves and the S waves, and a second signal having the T waves, and then mark a start of the Q waves and an end of the T waves for extracting the first signal and the second signal;
wherein through utilizing separate time points of the first signal having the reconstructed Q waves, R waves and S waves, the second signal of the T waves, the start of the Q waves, and the end of the T waves to determine whether there is a cardiovascular disease;
wherein the MAMA-EMD reconstruction firmware used for reconstructing the ECG signals is realized in a hardware circuit.

8. The multi-channel real-time cardiovascular performance evaluation system as claimed in claim 7, wherein the internal circuit of the multi-channel ECG signal processing device further comprises four input unit modules, each of the four input unit modules having a signal buffer, an amplifier, a filter, and a digital/analog converter connected in series.

9. The multi-channel real-time cardiovascular performance evaluation system as claimed in claim 7, wherein the internal circuit of the multi-channel ECG signal processing device further comprises a calculation and evaluation parameter unit, to determine whether there is the cardiovascular disease; and a communication unit, to be connected in a wired or wireless manner to a remote service platform through a network, to provide the signals synchronously to a medical unit.

\* \* \* \* \*